(12) United States Patent
Fu et al.

(10) Patent No.: US 11,016,082 B2
(45) Date of Patent: May 25, 2021

(54) NONINVASIVE DETECTION OF CANCER ORIGINATING IN TISSUE OUTSIDE OF THE LUNG USING EXHALED BREATH

(71) Applicant: University of Louisville Research Foundation, Inc., Louisville, KY (US)

(72) Inventors: Xiaoan Fu, Louisville, KY (US); Michael Nantz, Louisville, KY (US); Michael Bousamra, Louisville, KY (US); Victor van Berkel, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 419 days.

(21) Appl. No.: 15/223,756

(22) Filed: Jul. 29, 2016

(65) Prior Publication Data

US 2017/0030892 A1    Feb. 2, 2017

Related U.S. Application Data

(60) Provisional application No. 62/199,698, filed on Jul. 31, 2015.

(51) Int. Cl.

| | |
|---|---|
| *G01N 33/497* | (2006.01) |
| *A61B 5/08* | (2006.01) |
| *H01J 49/00* | (2006.01) |
| *H01J 49/38* | (2006.01) |
| *G01N 30/72* | (2006.01) |
| *G01N 33/543* | (2006.01) |
| *G01N 33/574* | (2006.01) |
| *G01N 33/64* | (2006.01) |
| *A61B 5/091* | (2006.01) |

(52) U.S. Cl.
CPC .......... *G01N 33/497* (2013.01); *A61B 5/082* (2013.01); *G01N 30/72* (2013.01); *G01N 33/543* (2013.01); *G01N 33/574* (2013.01); *G01N 33/57484* (2013.01); *G01N 33/64* (2013.01); *H01J 49/0031* (2013.01); *H01J 49/38* (2013.01); *A61B 5/091* (2013.01); *A61B 2505/03* (2013.01); *G01N 2033/4975* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 8,349,604 B2 | 1/2013 | Mohapatra et al. | |
| 8,491,494 B2 | 7/2013 | Kline | |
| 8,597,953 B2 | 12/2013 | Haick | |
| 2005/0085740 A1 | 4/2005 | Davis et al. | |
| 2008/0050839 A1 | 2/2008 | Suslick et al. | |
| 2011/0269632 A1* | 11/2011 | Haick | B82Y 15/00 506/7 |
| 2014/0244229 A1 | 8/2014 | Zhang et al. | |
| 2015/0064796 A1 | 3/2015 | Fu et al. | |

FOREIGN PATENT DOCUMENTS

| | | |
|---|---|---|
| WO | 2011049972 A1 | 4/2011 |
| WO | 2011083473 A1 | 7/2011 |
| WO | 2012135277 A1 | 10/2012 |

OTHER PUBLICATIONS

Mazzone, PJ, et al., Exhaled breath analysis with a colorimetric sensor array for the identification and characterization of lung cancer, 2012, J. Thorac. Oncol. 7:137-142.
Peled, N, et al., Non-invasive breath analysis of pulmonary nodules, 2012, J. Thorac. Oncol. 7:1528-1533.
Song, G, et al., Quantitative breath analysis of volatile organic compounds of lung cancer patients, 2010, Lung Cancer 67:227-231.
Horvath, I, et al., Exhaled biomarkers in lung cancer, 2009, Eur. Respir. J. , 34:261-275.
Peng, G, et al., Diagnosing lung cancer in exhaled breath using gold nanoparticles, 2009, Nat. Nanotechnol. 4:669-673.
Peng, G, et al., Detection of lung, breast, colorectal, and prostate cancers from exhaled breath using a single array of nanosensors, 2010, Br. J. Cancer 103:542-551.
Bajtarevic, A, et al., Noninvasive detection of lung cancer by analysis of exhaled breath, 2009, BMC Cancer 9:348-363.
Fuchs, P, et al, Breath gas aldehydes as biomarkers of lung cancer, 2010, Int. J. Cancer 126:2663-2670.
Poli, D, et al., Determination of aldehydes in exhaled breath of patients with lung cancer by means of on-fiber-derivatisation SPME-GC/MS, 2010, J. Chromatogr. B. Analyst, Technol, Biomed. Lice Sci. 878:2643-2651.
Phillips, M, et al., Detection of lung cancer using weighted digital analysis of breath biomarkers, 2008, Clin. Chem. Acta 393:76-84.
Lin, Y., et al., Protocol for Collection and HPLC Analysis of Volatile Carbonyl Compounds in Breath, Clinical Chemistry, American Association for Clinical Chemistry, Jan. 1, 1995, pp. 1028-1032, vol. 41, No. 7, Washington, D.C.

(Continued)

*Primary Examiner* — Jennifer Lamberski
(74) *Attorney, Agent, or Firm* — Dentons Bingham Greenebaum LLP; Brian W. Chellgren

(57) ABSTRACT

Provided is a non-invasive method of detecting or screening for a cancer in a subject specimen originating in a tissue outside of the lung. The method includes detecting elevated levels of one or more carbonyl-containing volatile organic compounds (VOCs) that are biomarkers for the cancer in exhaled breath from the subject specimen. The method may further include obtaining exhaled breath from the subject specimen; forming adducts of the carbonyl-containing VOCs with a reactive chemical compound; quantifying the adducts of the carbonyl-containing VOCs to establish a subject value for each of the adducts; and comparing each subject value to a threshold healthy specimen value for each of the adducts of the carbonyl-containing VOCs. One or more subject values at quantities greater than threshold healthy specimen values are also useful for screening for the cancer in the subject specimen.

14 Claims, 4 Drawing Sheets

(56) References Cited

OTHER PUBLICATIONS

Corradi, M., et al., Aldehydes in Exhaled Breath Condensate of Patients with Chronic Obstructive Pulmonary Disease, American Journal of Respiratory and Critical Care Medicine, Jan. 9, 2003, pp. 1380-1386, vol. 167, No. 10.
Wang, H., et al., Analysis of Low Molecular Weight Compounds by MALDI-FTICR-MS, Journal of Chromatography B: Biomedical Sciences & Applications, 2011, pp. 1166-1179, Elsevier, Amsterdam, NL.
Alfeeli, B., et al., "MEMS-Based Multi-Inlet/Outlet Preconcentrator Coated by Inkjet Printing of Polymer Adsorbents," Sensors and Actuators B 133, 2008, pp. 24-32.
Biswas, S., et al., "Nucleophilic cationization reagents," Tetrahedron Lett. 2010, pp. 1727-1729, vol. 51.
Deng, C., et al., "Determination of Acetone in Human Breath By Gas Chromatography-Mass Spectrometry and Solid-Phase Microextraction with On-Fiber Derivatization" J. Chromatogr. B 810, 2004, pp. 269-275.
Rexach, R., et al., "Quantification of O-glycosylation Stoichiometry and Dynamics Using Resolvable Mass Tags," Nature Chemical Biology, Sep. 2010, pp. 645-651, vol. 6.
Lamos, S., et al., "Relative Quantification of Carboxylic Acid Metabolites by Liquid-Chromatography Mass-Spectrometry Using Isotopic Variants of Cholamine," Anal Chem. Jul. 15, 2007, pp. 5143-5149, vol. 79, No. 14.
Higashi, T., et al. "Determination of prostatic androgens in 10 mg of tissue using liquid chromatography-tandem mass spectrometry with charged derivatization," Anal Bioanal Chem, 2005, pp. 1035-1043, vol. 382.
European Patent Office, International Search report in related PCT/US2012/030837, dated Jun. 26, 2012, 13 pages.
Barash et al., "Classification of Lung Cancer Histology by Gold Nanoparticle Sensors", Nanomedicine: Nanotechnology, Biology and Medicine 2012, 8, 580-589.
Bousamra et al., "Quantitative Analysis of Exhaled Carbonyl Compounds Distinguishes Benign from Malignant Pulmonary Disease", Journal of Thoracic Cardiovascular Surgery 2014, 148, pp. 1074-1081.
Fu et al., "Noninvasive Detection of Lung Cancer Using Exhaled Breath", Cancer Medicine 2014, 3, pp. 174-181.
Li et al., "A Microfabricated Preconcentration Device for Breath Analysis", Sensors and Actuators B: Chemical: International Journal Devoted to Research and Development of Physical and Chemical Transducers, Elsevier S.A., 2012, 7pp. 130-136.
Peled et al., Abstract A36: Breath Biomarkers in the Post NLST-era for the Discrimination between Malignant from Benign Pulmonary Nodules 2012, 18, pp. A36.
Hanai et al., "Analysis of Volatile Organic Compounds Released from Human Lung Cancer Cells and from the Urine of Tumor-Bearing Mice", 2012, 12, pp. 1-12.
Steeghs et al., "An Off-Line Breath Sampling and Analysis Method Suitable for Large Screening Studies", hysiological Measurement, Institute for Physics Publishing, Bristol, GB 2007, 28, pp. 503-514.
European Patent Office, International Search Report and Written Opinion in related PCT/US2014/053163, dated Nov. 30, 2015, 15 pages.
European Patent Office, International Search Report and Written Opinion in related PCT/US2016/044753, dated Nov. 8, 2016, 13 pages.
Xu, Yiwen et al.,"Detection and Identification of Breast Cancer Volatile Organic Compounds Biomarkers Using Highly-Sensitive Single Nanowire Array on a Chip" Journal of Biomedical Nanotechnology, vol. 9, No. 7, Jul. 1, 2013, pp. 1164-1172.
Amal, Haitham et al., "Assessment of Ovarian Cancer Conditions from Exhaled Breath" Obstetrical and Gynecological Survey, vol. 70, No. 2, Feb. 1, 2015, pp. 89-91.
Phillips, Michael et al., "Volatile Biomarkers in the Breath of Women with Breast Cancer" Journal of Breath Research, vol. 4, No. 2, Mar. 2, 2010, pp. 026003.
Phillips, Michael et al., "Prediction of Breast Cancer Using Volatile Biomarkers in the Breath" Breast Cancer Research and Treatment, Kluwer Academic Publishers, vol. 99, No. 1, Feb. 24, 2006, pp. 19-21.
Wang, Changsong et al., "Volatile Organic Metabolites Identify Patents with Breast Cancer, Cyclomastopathy, and Mammary Gland Fibroma" Scientific Reports, vol. 4, Jun. 20, 2014, 6 pp.
European Patent Office, Official Letter issued in corresponding European Patent Application No. 14762190.8 dated May 16, 2018, 9 pages.
Buszewski, Boguslaw, et al., "Investigation of lung cancer biomarkers by hyphenated separation techniques and chemometrics", Clinical Chemistry and Laboratory Medi, De Gruyter, DE, vol. 50, No. 3, Mar. 1, 2012 pp. 573-581, XP008173393.
Xu et al. Detection and Identification of Breast Cancer Volatile Organic Compounds Biomarkers Using Highly-Sensitive Single Nanowire Array on a Chip, Journal of Biomedical Nanotechnology, vol. 9, No. 7, Jul. 1, 2013, pp. 1165-1172.
Amal et al., assessment of Ovarian Cancer Conditions from Exhaled Breath, Obstetrical and Gynecological Survey, vol. 70, No. 2, Feb. 1, 2015, pp. 89-91.
Phillips, et al, Volatile biomarkers in the breath of women with breast cancer, Journal of Breath research, vol. 4, No. 2, Mar. 2, 2010, p. 026003.
Phillips et al, Prediction of breast cancer using volatile biomarkers in the breath, Breast Cancer Research and Treatment, Kluwer Academic Publishers, BO, vol. 99, No. 1, pp. 19-21.
Wang et al., Volatile Organic Metabolites Identify Patients with Breast Cancer, Cyclomastopathy, and Mammary Gland Fibroma, Scientific Reports, vol. 4, No. 20, Jun. 4, 2014, pp. 1-6.
International Search Report and Written Opinion issued in corresponding PCT Application No. PCT/US2016/044753, dated Nov. 8, 2016 (13 pages).

* cited by examiner

NONINVASIVE DETECTION OF CANCER ORIGINATING IN TISSUE OUTSIDE OF THE LUNG USING EXHALED BREATH

CROSS-REFERENCE TO RELATED APPLICATIONS

Pursuant to 37 C.F.R. § 1.78(a), this application claims the benefit of and priority to prior filed, co-pending Provisional Application Ser. No. 62/199,698 filed Jul. 31, 2015, which is expressly incorporated herein by reference in its entirety.

GOVERNMENT GRANT SUPPORT CLAUSE

This invention was made with Government support under Grant Award No. CBET-1159829 awarded by the National Science Foundation. The Government has certain rights in this invention.

FIELD

The present invention is directed to non-invasive methods for detecting and screening for cancer, and more particularly to a non-invasive method for detecting and screening for cancers in tissues outside of the lung, as well as cancers originating in tissues outside of the lung but that metastasize to the lung.

BACKGROUND

Cancers are a major cause of death worldwide, but early detection of cancer is a key factor for increasing survival rates of cancer patients. Currently, imaging and biopsy are the principal techniques used for cancer detection.

In recent years, the analysis of exhaled breath has become an international research frontier because of its applicability for noninvasive health diagnoses. Several approaches have been developed to analyze exhaled breath including the use of sensor arrays, proton-transfer reaction mass spectrometry (PTR-MS), selected ion flow tube mass spectrometry (SIFT-MS), and gas chromatography-mass spectrometry (GC-MS), to name a few. Although some volatile organic compounds (VOCs) in exhaled breath have been reported as potential lung cancer biomarkers, there has been no clinical adoption of breath analysis methods for diagnosis of cancers in tissues outside of the lung or in cancers originating in tissues outside of the lung but metastasizing to the lung.

Moreover, analyzing exhaled breath for cancer-indicating biomarkers, i.e., excreted metabolic products, is a daunting task, insofar as over 1700 endogenous VOCs have been identified in human breath. Additionally, many of these endogenous VOCs are present in exhaled breath in quantities that are less than the experimental error of the detection methods that are used to detect and/or identify them. For example, many of the VOCs in breath range from only a few parts per trillion (ppt) to a few parts per billion (ppb) concentration; many chemical species in breath samples are at millions-fold higher concentration than prevalent VOCs, such as water vapor and carbon dioxide, which may need to be removed to avoid swamping most analytical instruments. Additionally, breath is a chemically-diverse mixture containing analogue/homologue/isomeric mixtures of alcohols, ketones, and aldehydes, which complicate the identification of disease biomarkers; and VOCs in breath may include non-metabolic constituents, which may introduce false biomarkers in breath analysis.

Thus, in order to efficiently and accurately analyze VOCs in breath so as to detect or identify a disease state, there are multiple hurdles to overcome. The first hurdle to overcome is that of concentrating the VOCs of interest. General approaches to concentrating one or more VOCs of interest from dilute gaseous samples have focused on one of the following: chemical, cryogenic, and adsorptive methods. The second hurdle is identifying specific relationships between biomarker(s) and/or quantities of specific biomarkers, which can be correlated with a high level of certainty to the presence of the disease state, with a low chance of false-negatives.

Therefore, in view of the shortcomings and challenges with conventional methods of detecting/identifying and screening for cancer, there is a need for new non-invasive methods.

SUMMARY

Embodiments of the present invention provide a non-invasive method for detecting or screening for cancers originating in tissues outside of the lung.

According to one embodiment of the present invention, a non-invasive method of detecting or screening for a cancer disease state in a subject specimen is provided. The method includes quantifying levels of one or more carbonyl-containing volatile organic compounds (VOCs) that are biomarkers for cancer in exhaled breath from the subject specimen, and diagnosing the subject specimen as having a likelihood of the cancer disease state if the level of one or more of the carbonyl-containing VOCs is elevated above its respective threshold healthy specimen value. In one embodiment, the carbonyl-containing VOC is an adduct of a reactive chemical that is formed by a dehydration reaction. The carbonyl-containing VOC biomarker is selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds, which includes 2-pentanone and pentanal. The number of elevated biomarkers correlates to the likelihood of cancer, meaning more elevated biomarkers relates to increased likelihood of cancer.

According to another embodiment, a method of screening for a cancer disease state in a subject specimen is provided, the method comprising the steps of: obtaining exhaled breath from the subject specimen, wherein the exhaled breath includes a plurality of carbonyl-containing volatile organic compounds (VOCs); forming adducts of the plurality of carbonyl-containing VOCs with a reactive chemical compound; quantifying each of the adducts of each of the plurality of carbonyl-containing VOCs to establish a subject value for each of the adducts; and comparing each subject value to a threshold healthy specimen value for each of the adducts of the plurality of carbonyl-containing VOCs, the threshold healthy specimen value corresponding to values calculated from healthy specimens, in order to determine the presence of one or more subject values at quantities greater than their respective range of healthy specimen values, thereby indicating a substantial likelihood of a cancer disease state in the subject specimen. Exemplary types of cancer suitable for detection using the methods described herein are primary cancers that originate in tissues outside of the lung and may include primary cancers that metastasize to the lung. Exemplary primary cancers include, but are not limited to supraglottic squamous cell carcinoma, pancreatic cancer, melanoma, colon cancer, breast cancer, renal cell carcinoma, prostate cancer, ovarian cancer, esophageal cancer, chondrosarcoma, cholangiocarcinoma, lymphoma, and squamous skin cancer. In other embodiments, two or more, or three or more, or four or more subject values are elevated above their respective healthy specimen values.

In accordance with another embodiment, a non-invasive method of detecting a cancer disease state in a subject specimen is provided, the method comprising the steps of: concentrating a plurality of carbonyl-containing volatile organic compounds (VOCs) contained in exhaled breath obtained from the subject specimen, wherein the plurality of carbonyl-containing VOCs is selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds, which includes 2-pentanone and pentanal, which form adducts with a reactive chemical compound; quantifying the adducts of the plurality of carbonyl-containing VOCs to establish a subject value for each member of the adducts of the plurality of carbonyl-containing VOCs; and comparing the subject value for each member of the adducts of the plurality of carbonyl-containing VOCs to a threshold healthy specimen value for each member of the adducts of the plurality of carbonyl-containing VOCs to determine the presence of one or more subject values at quantities greater than its respective threshold healthy specimen value thereby indicating a substantial likelihood of the cancer disease state in the subject specimen. In another embodiment, two or more, or three or more, or four or more subject values are elevated above their respective healthy specimen values. In another embodiment, the plurality of carbonyl-containing VOCs is selected from the group consisting of 2-butanone, 2-hydroxyacetaldehyde, 3-hydroxy-2-butanone, and 4-hydroxy-2-hexenal.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to describe the invention.

DETAILED DESCRIPTION

Figure 1:
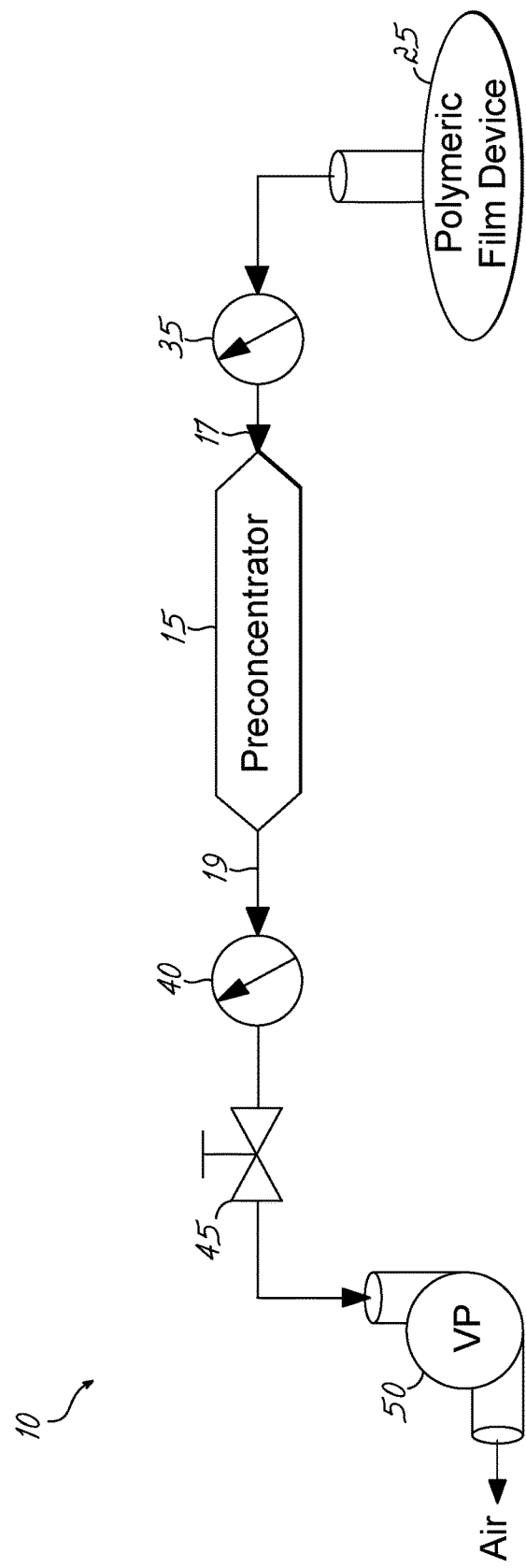
FIG. 1 is a schematic setup for concentrating carbonyl-containing VOCs in an air sample or a gaseous breath sample, in accordance with an embodiment of the present invention.

According to one embodiment of the present invention, a method of detecting or screening for a cancer disease state in a subject specimen is provided.

In one embodiment, the method includes detecting levels of one or more carbonyl-containing volatile organic compounds (VOCs) that are biomarkers for cancer in exhaled breath from the subject specimen, and diagnosing the subject specimen as having a likelihood of the cancer disease state if the level of one or more of the carbonyl-containing VOCs is elevated above its respective threshold healthy specimen value. In a preferred embodiment, adducts of the carbonyl-containing VOCs are analyzed. The adducts are formed by a dehydration reaction with a reactive chemical and advantageously permit the carbonyl-containing VOCs in exhaled breath to be preconcentrated prior to analytical testing. In accordance with embodiments of the present invention, the carbonyl-containing VOC biomarker is selected from the group consisting of 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds, which includes 2-pentanone and pentanal. The number of elevated biomarkers correlates to the likelihood of cancer, meaning more elevated biomarkers relates to increased likelihood of cancer.

In another embodiment, the method includes the steps of: obtaining exhaled breath from the subject specimen, wherein the exhaled breath includes a plurality of carbonyl-containing volatile organic compounds (VOCs); forming adducts of the plurality of carbonyl-containing VOCs with a reactive chemical compound; quantifying each of the adducts of each of the plurality of carbonyl-containing VOCs to establish a subject value for each of the adducts; and comparing each subject value to a range of healthy specimen values for each of the adducts of the plurality of carbonyl-containing VOCs, the range of healthy specimen values corresponding to values calculated from healthy specimens, in order to determine the presence of at least three subject values at quantities greater than their respective range of healthy specimen values, thereby indicating a substantial likelihood of a cancer disease state in the subject specimen. Exemplary types of cancer suitable for detection using the methods described herein are primary cancers that originate in tissues outside of the lung and may include primary cancers that metastasize to the lung. Exemplary primary cancers include, but are not limited to supraglottic squamous cell carcinoma, pancreatic cancer, melanoma, colon cancer, breast cancer, renal cell carcinoma, prostate cancer, ovarian cancer, esophageal cancer, chondrosarcoma, cholangiocarcinoma, lymphoma, and squamous skin cancer.

In accordance with embodiments of the present invention, the plurality of carbonyl-containing VOCs is selected from the group consisting of 2-butanone, 2-hydroxyacetaldehyde, 3-hydroxy-2-butanone, 4-hydroxy-2-hexenal ("4-HHE"), 4-hydroxy-2-nonenal ("4-HNE"), and a mixture of $C_5H_{10}O$ compounds that includes 2-pentanone and pentanal.

As used herein, "healthy specimen" is defined as a specimen that does not have any detectable cancer (as determined by standard methods of detecting cancer including CT scans and physical examination) and does not have a diagnosable cancer disease state.

As used herein, "subject specimen" is defined as the specimen from which a sample of exhaled breath is obtained for the purpose of diagnosing or screening the presence/absence of a cancer disease state. The subject specimen may have been previously screened using a computerized tomography (CT), where a suspicious lesion or nodule was detected, and a higher specificity (true negative) test is favored that utilizes two or more, or three or more biomarker values above its respective threshold healthy specimen value. For screening purposes, the subject specimen may not have been screened using a CT scan, but may have other risk factors (e.g., known exposure to carcinogens, family history of cancer, or genetic markers) and a higher selectivity (true positive) test is favored that utilizes one or more biomarker values above its respective threshold healthy specimen value.

As used herein, "threshold healthy specimen value" means a value determined by performing the testing method on a plurality of healthy specimens, wherein a subject value exceeding the determined threshold healthy specimen value indicates a cancer disease state.

As used herein, "substantial likelihood of a cancer disease state" means that the probability that the cancer disease state exists in the subject specimen is about 80% or more, based on the confidence levels of the testing method, whereas "likelihood of a cancer disease state" means that the probability that the cancer disease state exists in the subject specimen is about 50% or more, based on the confidence levels of the testing method. Of course, intermediate levels of likelihood are further contemplated, such as about 60% or more, or about 70% or more.

As used herein, "adducts" or "conjugates" denotes the reaction product of a reactive chemical compound and the carbonyl-containing VOCs cancer biomarker. These adducts are formed by a dehydration reaction of an aldehyde or a ketone, which transforms the volatile cancer biomarker into an unnatural, non-volatile chemical compound.

As previously noted above, breath analysis is a developing modality with potential to simplify the workup of suspected cancer. However, until the discovery of the present invention, no method has demonstrated clinical utility due to multiple factors, such as extremely low concentrations of involved carbonyl-containing VOC biomarker compounds, complexities in the isolation process of these compounds, and the lack of a diagnostic algorithm useful to clinicians. Embodiments of the present invention are focused on select carbonyl-containing VOCs, such as 2-butanone, 2-hydroxyacetaldehyde, 3-hydroxy-2-butanone, 4-hydroxy-2-hexenal, 4-hydroxy-2-nonenal, and/or a mixture of $C_5H_{10}O$ compounds that includes 2-pentanone and pentanal.

In accordance with embodiments of the present invention, the method of detecting cancer includes the selective capture and concentration of certain cancer biomarkers, i.e., the carbonyl-containing VOCs, which may be achieved by passage of exhaled breath through a chemical preconcentrator assembly 10, which includes a chemical preconcentrator 15 having an inlet 17 and an outlet 19 that permit passage of the exhaled breath sample there through, as shown in FIG. 1. The assembly 10 further includes an inflatable polymeric film device 25 which may be fluidly coupled to a flowmeter 35 prior to the inlet 17 of the chemical preconcentrator 15. The outlet 19 of the chemical preconcentrator 15 may be fluidly coupled to a pressure gauge 40, a valve 45, and a vacuum pump 50, as described in more detail below.

One or more samples of exhaled breath from a subject specimen may be collected in the inflatable polymeric film device 25. One exemplary inflatable polymeric film device suitable for exhaled breath sample collection is a one liter Tedlar® gas sampling bag (Sigma-Aldrich Co., LLC, St. Louis, Mo.), which includes a Teflon® valve. For sample collection, the subjects may directly exhale into the Tedlar® gas sampling bag through the Teflon® valve, which provides a non-invasive collection technique.

The flow meter 35 is not particularly limited to any specific type of flow meter. Advantageously, the flow meter 35 should be capable of accurately measuring the volume of gas entering the chemical preconcentrator 15, which can permit quantifying the concentration of the carbonyl-containing VOCs in the exhaled breath samples.

The pressure gauge 40, the valve 45, and the vacuum pump 50 are similarly not particularly limited to any specific type. The vacuum pump 50 pulls a vacuum, which may be modulated or isolated from the chemical preconcentrator 15 by adjusting the valve 45. The pressure gauge 40 may be used to indicate proper functioning and/or operation of the vacuum pump 50 and the entire chemical preconcentrator assembly 10.

As noted above, the concentration levels of many biomarkers in exhaled breath are below detection limits of many standard analytical techniques. However, utilizing the chemical reactivity of the carbonyl functional group of aldehydes and ketones with certain reactive chemicals, the carbonyl-containing VOCs in exhaled breath can be preconcentrated prior to analysis. Accordingly, one suitable preconcentrator 15 useful for preconcentrating the carbonyl-containing VOCs in exhaled breath is described in U.S. Pat. No. 8,663,581, which is incorporated herein in its entirety and further described herein. It should be appreciated that while the preconcentrator and methods embodied within the teachings of U.S. Pat. No. 8,663,581 were employed in embodiments of the present invention described herein, the invention is not particularly limited thereto. Other preconcentrator devices and/or methods may be utilized, so long as the devices and methods are effective in preconcentrating the requisite carbonyl-containing VOCs in exhaled breath to provide analytical samples.

Thus, in accordance with an embodiment, the chemical pre-concentrator 15 may include a support structure and a layer of a reactive chemical compound on a surface of the support structure. As used herein, the phrase "reactive chemical compound" includes molecular compounds held together by covalent bonds and salts held together by ionic bonds. The reactive chemical compound form conjugates or adducts with the carbonyl-containing VOCs in order to affect the collecting and pre-concentrating. As used herein, "carbonyl-containing" refers to aldehydes and ketones.

In general terms, the reactive chemical compounds include a reactive terminus capable of reacting with a carbonyl functional group on the VOC of interest; an anchoring moiety capable of reversibly effecting the formation of a layer on the surface of the support structure, and a linking group between the reactive terminus and the anchoring moiety. As represented in Formula (I) below, the reactive terminus includes an amino group ($NH_2$) bonded to a heteroatom (Z), a linking group (L), and an anchoring moiety (Y), wherein Z, L, and Y are defined below. In accordance with embodiments of the present invention the reactive chemical compound has a general formula according to that of Formula (I):

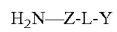
Formula (I)

wherein Z is NH, NR or O; L is a linking group; and Y is di-substituted or tri-substituted N or P moiety; R is selected from the group consisting of alkyls, aralkyls, aralkenyls, and aralkynyls, each of which may be substituted or unsubstituted, and optionally contain one or more heteroatoms.

According to an embodiment, Y can be $-NR^1R^2$, or $-NR^1R^2R^3$, $-PR^1R^2$, $-PR^1R^2R^4$, wherein $R^1$, $R^2$, $R^4$ are independently selected from the group consisting of alkyls, aralkyls, aralkenyls, and aralkynyls, each of which may be substituted or unsubstituted, and optionally contain one or more heteroatoms; and $R^3$ is selected from the group consisting of H, alkyls, aralkyls, aralkenyls, and aralkynyls, each of which may be substituted or unsubstituted, and optionally contain one or more heteroatoms. In an alternative embodiment, $R^1$ and $R^2$ in combination can also form a heterocyclic ring, such as a piperidine or a morpholine moiety.

According to another embodiment of the invention, the reactive chemical compound may include a reactive terminus, a cationic moiety and a linking group L therebetween. When Y is —$NR^1R^2R^3$ or —$PR^1R^2R^4$, the reactive chemical compound is a cationic salt, which may further comprise $^-A$, which is an anionic counter-ion. Accordingly, the cationic moiety may comprise a cationic nitrogen, such as an ammonium ion, or a cationic phosphorus, such as a phosphonium.

When Y is phosphorus, $R^1$, $R^2$ and $R^4$ may all be an aryl group, such as phenyl. When Y is nitrogen, $R^1$, $R^2$ and $R^3$ may be alkyls, each of which may be substituted or unsubstituted, and optionally contain one or more heteroatoms. In an alternative embodiment, when Y is nitrogen, $R^1$, $R^2$ may be alkyls, each of which may be substituted or unsubstituted, and optionally contain one or more heteroatoms, and $R^3$ may be H.

According to embodiments of the invention, the reactive terminus may comprise a hydrazine or aminooxy group. For example, Z may be nitrogen, such as NH or NR, thereby forming a hydrazine terminus. Alternatively, Z may be oxygen, thereby forming an aminooxy terminus. The hydrazine or aminooxy termini form the reactive functional group of the reactive chemical compounds, and as such, the aldehydes and ketones react with the hydrazine or the aminooxy functional groups via a dehydration or condensation reaction. Accordingly, the reactive terminus of the reactive chemical and the carbonyl functionality of the VOC are complementary reactants to the condensation reaction that forms adducts of the carbonyl-containing VOC cancer biomarkers.

According to embodiments of the present invention, the conjugates or adducts formed between the reactive chemical compounds of formula (I) are hydrazones (when Z=N) or oximes (when Z=O). In either adduct form, the covalent bonding fixes the VOC to the anchoring moiety and thereby pre-concentrates the carbonyl-containing VOC cancer biomarkers prior to analysis.

In the reactive chemical compound, the linking group L covalently bonds the reactive terminus to the anchoring moiety. The reactive chemical compounds are not particularly limited by their linking group. However, increased substitution in the proximity of the reactive terminus may increase steric hindrance and thereby affect the reactivity of the compound. As such, varying the substitution may enable differentiation between aldehyde and ketone analytes, if desired. According to embodiments of the invention, the linking group may include a non-ionic segment, which may be a substituted or unsubstituted alkyl, a substituted or unsubstituted aryl, or an ether. For example, the linking group L may be ethyl, propyl, butyl, pentyl, hexyl, heptyl, or octyl segment. The linking group L may include an ether, such as polyethyleneglycol (PEG).

When the reactive chemical compound is a salt, the anionic member (A) of the reactive chemical compound is a negatively-charged species which counterbalances the positively-charged moiety. According to another embodiment, A may be a conjugate base of a strong acid. For example, A may be a halide such as bromide or chloride. According to another embodiment, A may be a conjugate base of a weak acid. For example, A may be a carboxylate such as benzoate.

In one embodiment, Z is O, and Y is nitrogen, and the reactive chemical compound has a general formula according to that of Formula (II):

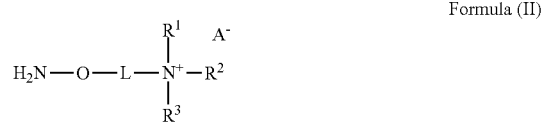

Formula (II)

where L, $R^1$, $R^2$, $R^3$, and A are defined above. In another embodiment, at least one of $R^1$, $R^2$ and $R^3$ is a methyl group and A is a halide.

It is also envisaged that the reactive chemical compound can include a plurality of reactive termini. For example, at least one of $R^1$, $R^2$ and $R^3$ may be a substituted or unsubstituted alkyl including at least two heteroatoms, and having a general formula of -$L^1$-Z—$NH_2$, wherein $L^1$ is a linking group between an ammonium nitrogen and Z.

As shown in Scheme 1, an exemplary reactive chemical compound (4), according to Formula (II) where L is ethyl, may be realized via a three step synthetic sequence. An amino alcohol (1) may be converted to the corresponding phthaloyl-protected aminooxy ammonium salt (3) by first treating the amino alcohol (1) with N-hydroxyphthalimide (2) under Mitsunobu conditions, which is subsequently followed by quaternization using an alkyl halide ($R^3$-X) to provide the protected salt (3). Removal of the phthaloyl group via hydrazinolysis affords the reactive compound (4). Exemplary reactive chemical compounds are shown in Table 1 below.

Scheme 1: Synthesis of aminooxy reactive compound (4) (Ph$_3$P is triphenylphosphane; DEAD is diethyl azodicarboxylate).

TABLE 1

Exemplary reactive chemical compounds 4a-4e prepared according to a three-step synthetic sequence.

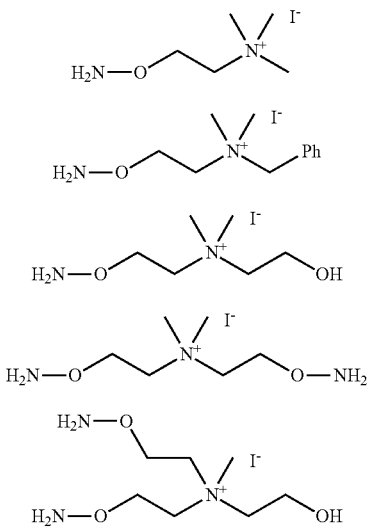

In yet another embodiment, Z is O, and Y is nitrogen, and the reactive chemical compound has a general formula according to that of Formula (III):

Formula (III)

The reactive chemical compounds in accordance with general Formula (III) can be prepared by omitting the quaternization step (2) in the synthetic sequence shown in Scheme I. For example, an exemplary reactive chemical compound according to Formula (III) where L is ethyl, may be realized via a two step synthetic sequence. Amino alcohol (1) may be converted to its corresponding phthaloyl-protected aminooxy by first treating the amino alcohol (1) with N-hydroxyphthalimide (2) under Mitsunobu conditions. Removal of the phthaloyl group via hydrazinolysis affords the tertiary amine reactive compound according for Formula (III). An exemplary tertiary amine reactive compound is N-(2-(aminooxy)ethyl)-morpholine (AMA).

According to an embodiment, the tertiary amine group can be used as an anchoring group. In an alternative embodiment, the tertiary amine reactive chemical compound may be converted to its Brønsted salt by treatment with a protic acid. For example, the tertiary amine reactive chemical compounds of Formula (III) can be dissolved in a suitable organic solvent and treated with an acid to prepare the reactive chemical compound of Formula (II), where $R^3$ is H, and A is the conjugate base of the acid.

The reactive chemical compounds may be dissolved in one or more solvents and then deposited on a surface of a support structure. The solvent is not particularly limited, but should be capable of evaporating while leaving the reactive chemical compound on the surface of the support structure. Suitable solvents include polar protic solvents, polar aprotic solvents, or combinations thereof. Exemplary polar protic solvents include, but are not limited to, water and alcohols, such as methanol and/or ethanol. Exemplary polar aprotic solvents include, but are not limited to acetonitrile, dimethylformamide, dimethylsulfoxide and nitromethane. The reactive chemical compound may be provided as a liquid, obtained by combining the reactive chemical compound and at least one solvent, which is then applied to a surface of a support structure. Removal of the solvent thereby deposits the reactive chemical compound on the surface of the support structure as a layer.

The support structures of the chemical pre-concentrators, in accordance with embodiments of the present invention, provide a surface to which the reactive chemical compound can be retained after solvent removal. A binding force that contributes to retaining the reactive chemical compound on the surface of the support structure is the interaction between the anchoring moiety (e.g., ammonium group) portion of the reactive chemical compound and the functional groups on the surface of the support structure, such as hydroxyls, as discussed further below.

The configuration of the support structure is not particularly limited by any specific configuration, but when present, features such as inlet and outlet structure, shapes and array patterns may affect the efficiency of the reactive chemical compound to capture the desired chemical analytes. Accordingly, the support structure may be configured to optimize surface area and flow dynamics.

Figure 2A:
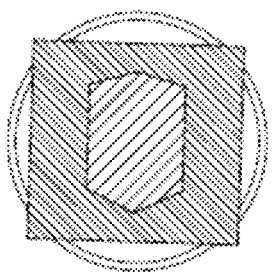
FIG. 2A is a photograph showing a preconcentrator connected to two fused silica tubes that is suitable for use in the schematic shown in FIG. 1; the preconcentrator is shown place on a U.S. dime to indicate its size.
Figure 2B:
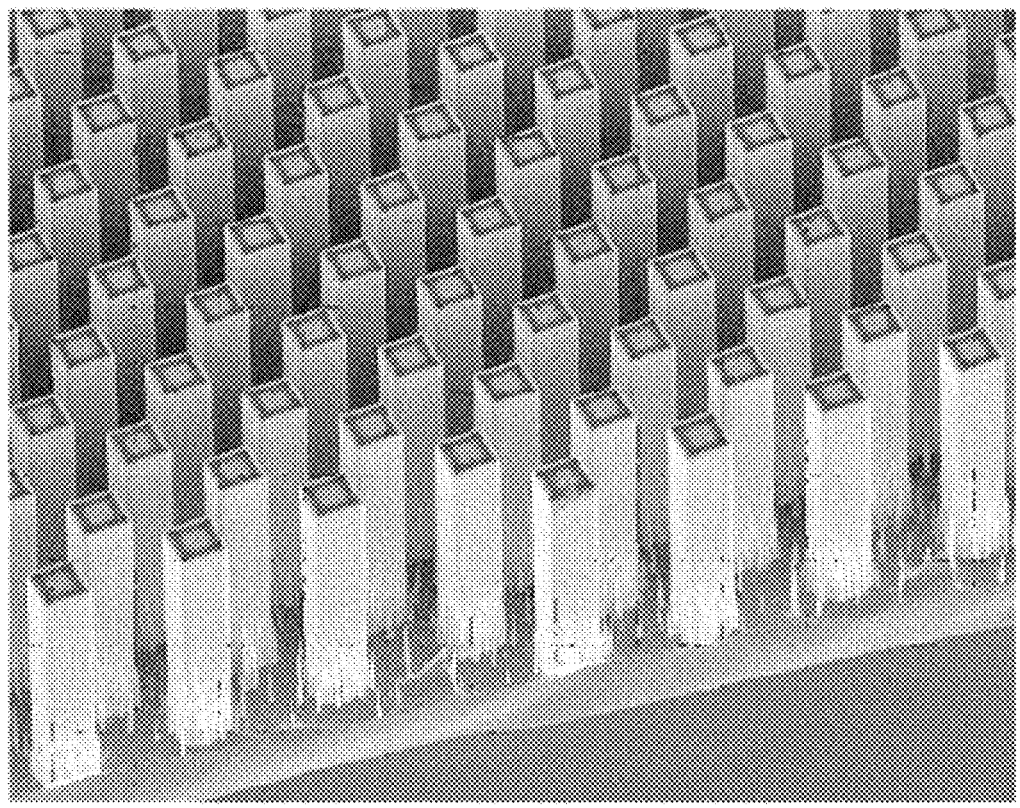
FIG. 2B is a scanning electron micrograph showing a micropillar array within the preconcentrator shown in FIG. 2A.
Figure 3:
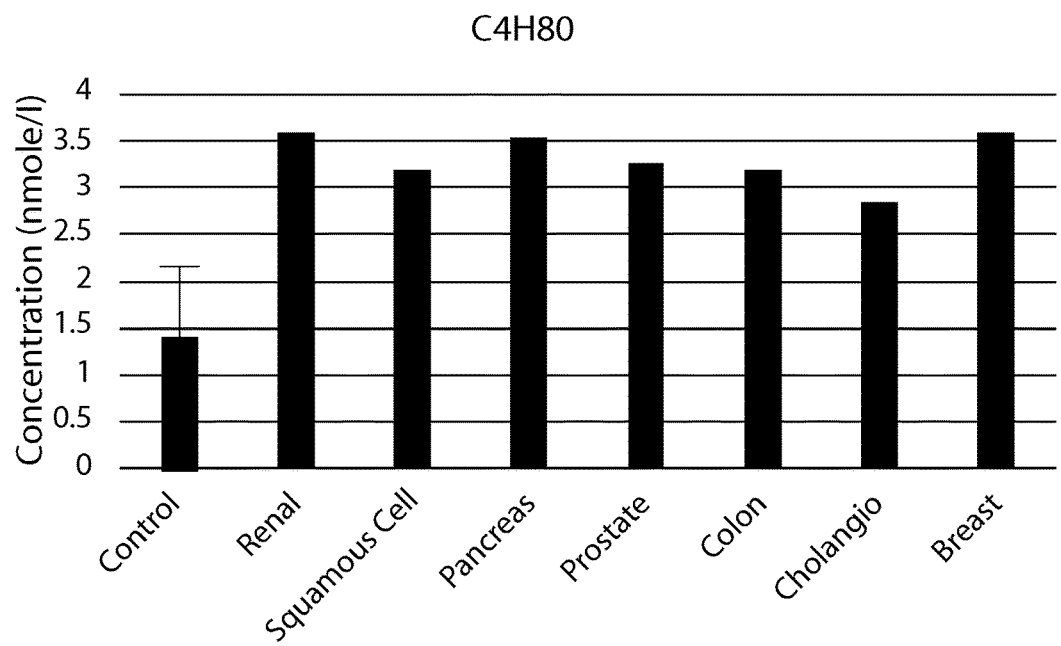
FIG. 3 is a graph comparing the levels of $C_4H_8O$ in subjects having a variety of cancer types with healthy control subjects.
Figure 4:
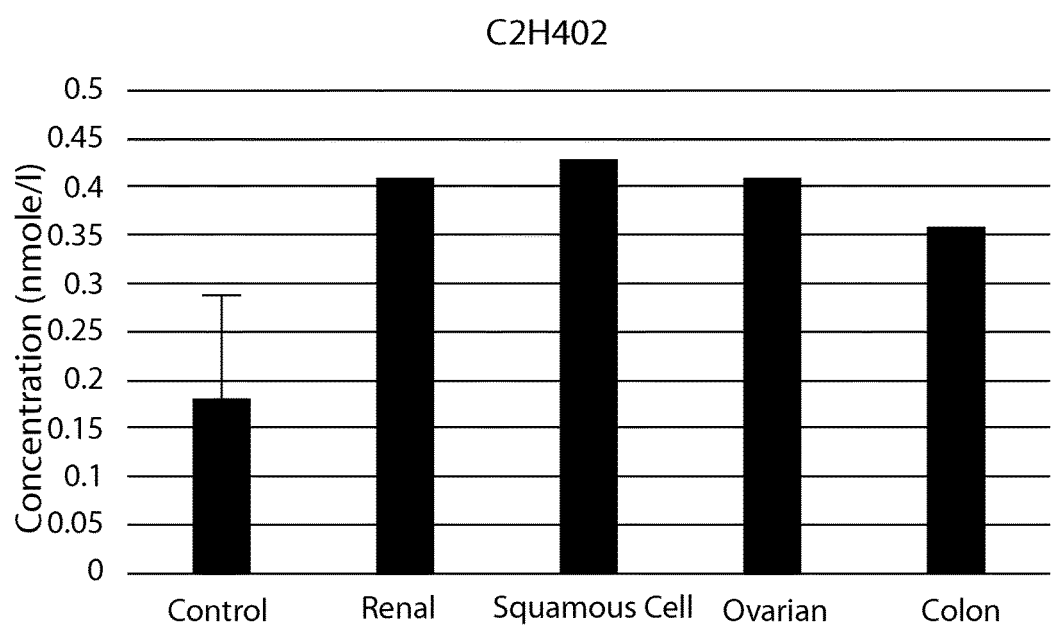
FIG. 4 is a graph comparing the levels of $C_2H_4O_2$ in subjects having a variety of cancer types with healthy control subjects.
Figure 5:
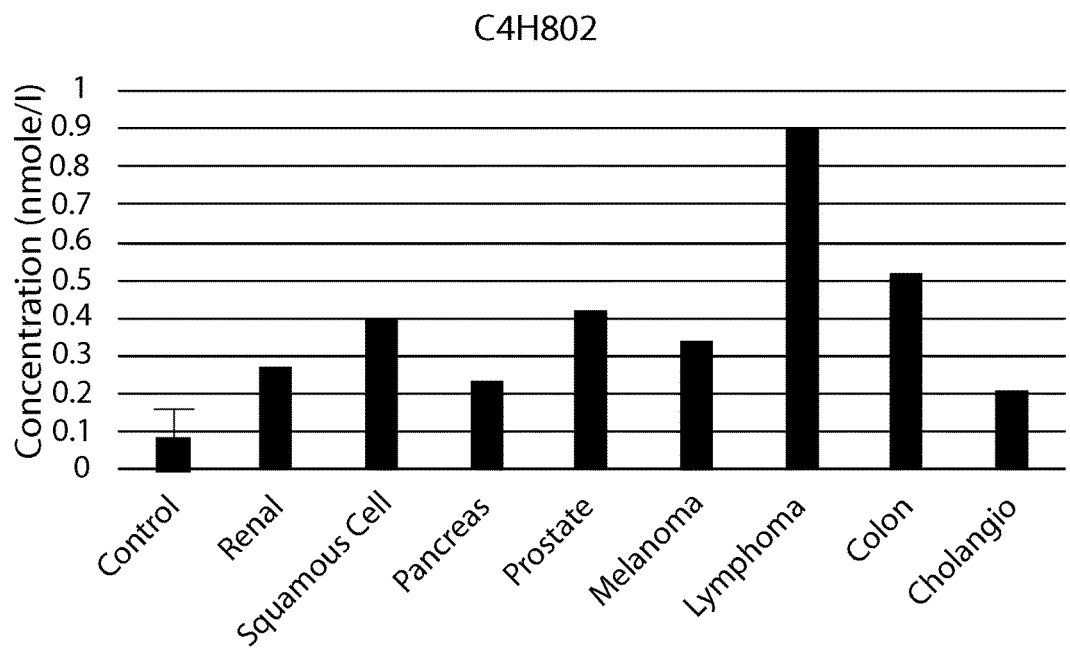
FIG. 5 is a graph comparing the levels of $C_4H_8O_2$ in subjects having a variety of cancer types with healthy control subjects.
Figure 6:
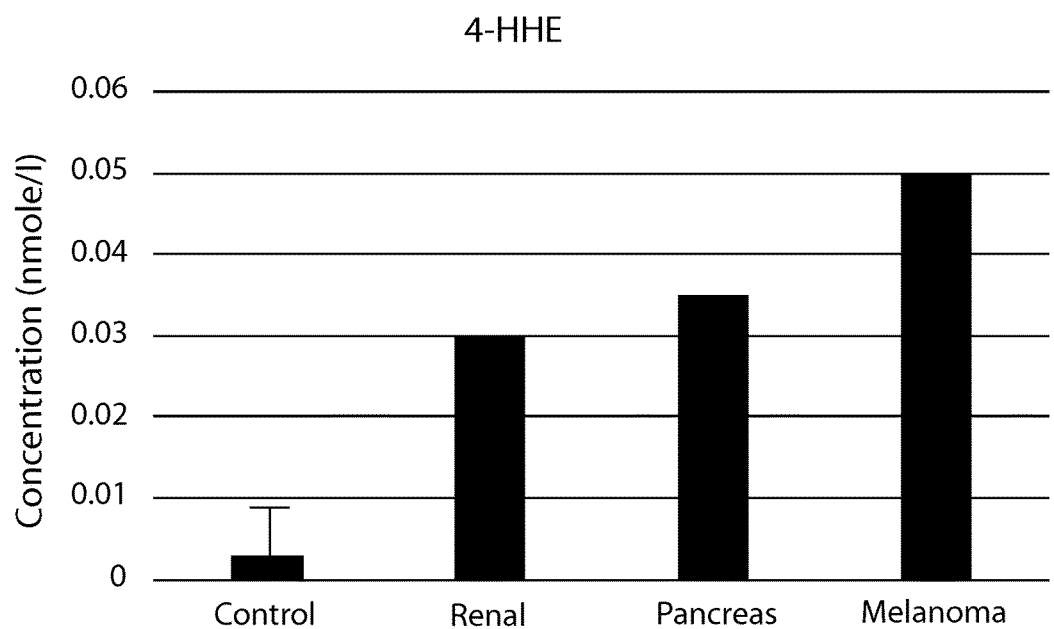
FIG. 6 is a graph comparing the levels of 4-HHE in subjects having a variety of cancer types with healthy control subjects.

In reference to FIG. 2A, a photograph is provided showing a preconcentrator connected to two fused silica tubes, which is shown placed on a U.S. dime to indicate its size. In FIG. 2B, a scanning electron micrograph is provided showing a micropillar array within the preconcentrator shown in FIG. 2A. Other surface configurations of the pre-concentrator may be used.

The support structure may comprise any material that is compatible with the reactive chemical compound and is substantially insoluble in the solvent vehicle used to deposit the compound. More particularly, the surface of the support structure, which may be the same as or different from the underlying portion of the support structure, may comprise a material selected from the group consisting of dielectrics and semiconductors, which facilitates using MEMS techniques for manufacture. For example, the surface material may be silicon, polycrystalline silicon, silicon oxide, silicon nitride, silicon oxynitride, silicon carbide, titanium, titanium oxide, titanium nitride, titanium oxynitride, titanium carbide, aluminum, aluminum oxide, aluminum nitride, aluminum oxynitride, aluminum carbide, or combinations thereof. Advantageously, the reactive chemicals compounds show exceptional binding to support structure surfaces comprising silicon oxide, titanium oxide, aluminum oxide, or combinations thereof.

The surface of the support structure may affect the binding forces for adhering the reactive chemical compound to the support structure. For example, the thermal oxidation of the silicon surface of the wafer or the deposition of silicon dioxide may control the density of silanol groups and/or the electrostatic charge on the $SiO_2$ surface of the micropillars.

The chemical pre-concentrator 15 may further comprise a housing surrounding the support structure, wherein the housing has an inlet 17 and an outlet 19. According to an embodiment, the chemical pre-concentrator includes an airflow conduit directed at the surface of the support structure. Airflow conduits can include tubular devices, which are not attached to the support structure, or maybe fabricated into the support structure. The outlet 19 and/or the inlet 17 may be configured to couple with a sampling pump to thereby facilitate the transfer of a portion of a gaseous sample outside of the housing into the housing through the inlet.

The reactive chemical compound may be applied to the surface of the support structure by any suitable method. In one embodiment, a liquid comprising a first solvent and the reactive chemical compound is contacted with the surface of the support structure and the first solvent is removed by evaporation under reduced pressure. If desired, the first solvent may be evaporated in a vacuum oven. For example, a dilute solution of a reactive chemical compound can be prepared from about 3.5 mg of the reactive chemical compound dissolved in about 0.5 mL of a first solvent, which simply acts as a carrier solvent. About 10 µL to about 20 µL of the dilute solution is applied to the pre-concentrator, and then the first solvent is removed under reduced pressure to afford a loading of approximately 0.07 to 0.14 mg of the reactive chemical compound into the pre-concentrator. After the removal of the first solvent, the chemical preconcentrator is ready for concentrating the carbonyl-containing VOC biomarkers.

In practice, a measured volume of an exhaled breath sample is passed through the chemical preconcentrator and the carbonyl-containing VOCs form adducts with the reactive chemical, which are retained on the surface of the support structure, thereby effectively providing a concentrated sample of the adducts. After the exposure is discontinued, the chemical preconcentrator may be treated with a second solvent capable of dissolving the VOC adducts to facilitate removal of the VOC adducts from the surface of the support structure and provide a concentrated sample of the VOC adducts for analytical testing. Suitable solvents include polar protic solvents, polar aprotic solvents, or combinations thereof. Exemplary polar protic solvents include, but are not limited to, water and alcohols such as methanol. Exemplary polar aprotic solvents include, but are not limited to, acetonitrile, dimethylformamide, dimethylsulfoxide and nitromethane. If desired, the eluted concentrated sample may be further concentrated by evaporating at least a portion of the second solvent.

At least a portion of the concentrated sample of the VOC adducts may be analyzed to identify and quantify the VOC adducts. One exemplary analytical tool is mass spectrometry, which may be performed with or without chromatography. For example, the conjugate may be analyzed using high performance liquid chromatography coupled with mass spectrometry (HPLC-MS) or gas chromatography coupled with mass spectrometry (GC-MS). Neutral chemical conjugates, such as those that can be obtained using tertiary amine reactive chemical compounds according to general Formula (III) are amenable to analysis using GC-MS. One beneficial feature of the tertiary amine reactive chemical compounds is their capability to be protonated with acid and form a positive charge, which is especially well-suited for analysis by Fourier transform ion cyclotron resonance-mass spectrometry (FT-ICR-MS), discussed below. By comparing FT-ICR-MS and GC-MS results, all ketones and aldehydes adducts can generally be identified and/or quantified. It should be appreciated that other analytical techniques, e.g., laser spectroscopy, etc., may also be useful toward quantifying the biomarker adducts. Internal standards may also be utilized to assist in the identification and/or quantification process.

Where the reactive chemical compound utilized is a cationic salt according to general Formula (II), another useful method of analyzing the conjugate is FT-ICR-MS. The cationic functionality also imparts exceptionally high sensitivity for [+] ion FT-ICR-MS using nanoelectrospray techniques. This exceptionally high sensitivity enables detection limits in the femtomole to attomole ranges. This sensitivity is orders of magnitude better than even the most sensitive GC-MS, which generally requires 100-1,000 femtomoles or more for detection. Moreover, because the VOCs are rendered non-volatile, the final analytical solution can be concentrated (e.g., to dryness) and taken up by a very small amount of solvent. Additionally, nanoelectrospray FTMS only needs a few microliters of sample volume.

Moreover, FT-ICR-MS may also be coupled with chemical ionization (CI) or photo ionization (PI) and operated in negative [−] ion mode. Operating in [−] ion mode, rejects the cationic phase and permits the analysis of other chemicals retained in the chemical pre-concentrator. In either mode, the VOC adducts of the reactive chemical compound may be desorbed from the structure support surface of the pre-concentrator by dissolution with solvent followed by direct FT-ICR-MS analysis.

The concentrated samples of the carbonyl-containing VOC adducts, which can be obtained from healthy specimens and subject specimens, can be analyzed using FT-ICR-MS and quantified. The analytical results can then be compared between the specimen groups using statistical methods, such as the Wilcoxon test to determine statistically significant differences between the specimen groups. According to embodiments of this invention, specific carbonyl-containing VOC biomarkers (i.e., 2-butanone, 2-hydroxyacetaldehyde, 3-hydroxy-2-butanone, 4-hydroxy-2-hexenal, 4-hydroxy-2-nonenal, and a mixture of $C_5H_{10}O$ compounds that includes 2-pentanone and pentanal) have been identified to be present at elevated levels in exhaled breath of cancer patients (subject specimens) with different types of primary cancers that originate in tissues outside of the lung and may include primary cancers that metastasize to the lung. Exemplary primary cancers include, but are not limited to supraglottic squamous cell carcinoma, pancreatic cancer, melanoma, colon cancer, breast cancer, renal cell carcinoma, prostate cancer, ovarian cancer, esophageal cancer, chondrosarcoma, cholangiocarcinoma, lymphoma, and squamous skin cancer.

Herein we describe a quantitative analysis, using silicon microreactors chemical preconcentrators for the capture of carbonyl-containing VOCs, that forms adducts of the carbonyl-containing VOCs contained in exhaled breath, and the identification/quantification of specific carbonyl-containing VOCs that are related to cancer histology. The method described herein only requires a subject patient to provide a sufficient quantity of exhaled breath, such as filling a one-liter Tedlar bag with exhaled breath. The exhaled breath sample can then be further processed and quantitatively analyzed, for example by mass spectrometry.

Without being bound to any one particular theory, the methods described herein are premised on the believed principle that cancer induces oxidative stress and oxidase enzymes, and this in turn produces higher concentrations of specific carbonyl-containing VOCs that are released into the blood and travel to the lungs where the carbonyl-containing VOCs are exhaled in the breath. Carbonyl-containing VOCs are produced in biochemical pathways as intermediates, and some can be unique to a given pathway, such as lipid oxidation induced by free radicals. Therefore, the investigation focused on identification of carbonyl-containing VOC cancer biomarkers in exhaled breath using the silicon microreactor chemical preconcentrator technology that we previously developed for capture and analysis of trace carbonyl VOC in air and exhaled breath.

Non-limiting examples of a method for detecting a cancer disease state, in accordance with the description, are now disclosed below. These examples are merely for the purpose of illustration and are not to be regarded as limiting the scope of the invention or the manner in which it can be practiced. Other examples will be appreciated by a person having ordinary skill in the art.

EXAMPLES

The Chemical Preconcentrator.

The chemical preconcentrators (or silicon microreactors) were fabricated from 4"-silicon wafers using standard microelectromechanical systems (MEMS) fabrication techniques, such as described in Li, M. et al. (2012) *Preconcentration and Analysis of Trace Volatile Carbonyl Compounds, Anal. Chem.* 84:1288-1293 and U.S. Pat. No. 8,663,581. The microreactor (FIG. 2A) includes of an array of micropillars defining microfluidic channels (seen in FIG. 2B). The micropillars have a high-aspect-ratio with dimensions of 50 µm×50 µm×250 µm created by dry reactive ion etching (DRIE). The distance from center to center of the micropillars is 100 µm. The channel size is 7 mm×5 mm, with a total volume in the microreactor of about 5 µL. The microreactor includes over five thousand square micropillars corresponding to a total micropillar surface area of about 260 $mm^2$. The inlet and outlet of the microreactor were fitted with 190 µm O.D., 100 µm I.D. deactivated fused silica tubes using a silica-based bonding agent (see FIG. 2A).

The surface functionalization of the channels and micropillars with 2-(aminooxy)-N,N,N-trimethylethanammonium (ATM) iodide (Structure 4a in Table 1) was performed by injecting ATM iodide in methanol solution of known concentration into the microreactor from one connection port followed by evaporation of the solvent under vacuum. The slightly negative surface charge of the silicon oxide micropillars allows for electrostatic binding of the cationic ATM on the surfaces of the micropillars. ATM reacts chemoselectively with trace carbonyl-containing VOCs in exhaled breath by means of oximation with high reactivity.

Exhaled Breath Specimen Collection and Processing.

Air and exhaled breath samples were collected in one liter Tedlar® bags (Sigma-Aldrich, USA). The detailed research protocol for collection of exhaled breath samples was approved by the Institutional Review Board (IRB) at the University of Louisville. Exhaled breath samples of healthy controls (n=193) and patients with various types of primary cancers originating outside of the lung (n=32) were analyzed and the concentrations of all carbonyl-containing compounds were determined. All clinical diagnosis of patients with primary cancers originating outside of the lung were made independent of the collection of the exhaled breath samples.

For the sample collection of exhaled breath, subjects would directly exhale breath into Tedlar® bags through the Teflon® tip, thus providing a non-invasive collection technique that was readily accepted by the patients. After collection of exhaled breath, the Tedlar® bags were connected to the inlet port of the microreactor through one fused silica tube. The exit port of the microreactor was connected to a vacuum pump through the other fused silica tube on the microreactor as shown in FIG. 2A. The analysis assembly 10, shown in FIG. 1, for capture of carbonyl-containing VOCs includes a vacuum pump 50 to pull gaseous breath samples from the Tedlar® bag through the ATM-coated preconcentrator 15. After the exhaled breath sample had been pulled through the preconcentrator 15 and evacuated by vacuum, the preconcentrator 15 was disconnected. Finally, the ATM-VOC adducts were eluted from the preconcentrator 15 with 100 µL cold methanol to afford 99% ATM-VOC recovery. The eluted solution was directly analyzed by FT-ICR-MS. A known amount of ATM-acetone-d6 in methanol was added to the eluent as an internal standard. The concentrations of all carbonyl compounds in exhaled breath were determined by comparison of the relative abundance with that of added ATM-acetone-d6 as the internal standard reference.

FT-ICR-MS Instrumentation.

The eluent was analyzed by a hybrid linear ion trap-FT-ICR-MS (Finnigan LTQ FT, Thermo Electron, Bremen, Germany) equipped with a TriVersa NanoMate ion source (Advion BioSciences, Ithaca, N.Y.) with an electrospray chip (nozzle inner diameter 5.5 µm). The TriVersa NanoMate was operated in positive ion mode by applying 2.0 kV with no head pressure. Initially, low resolution MS scans were acquired over 1 minute to ensure the stability of ionization, after which high mass accuracy data was collected using the FT-ICR analyzer. FT-MS scans were acquired for 8.5 min at a target mass resolution of 100,000 at 800 m/z. The AGC (automatic gain control) maximum ion time was set to 500 ms (but typically utilized <10 ms) and five "µscans" were acquired for each saved spectrum; thus the cycle time for each transformed and saved spectrum was about 10 seconds. FT-ICR mass spectra were exported as exact mass lists into a spreadsheet file using QualBrowser 2.0 (Thermo Electron), typically exporting all of the observed peaks. ATM and ATM-VOC adducts were assigned based on their accurate mass by first applying a small (typically <0.0005) linear correction based on the observed mass of the internal standard.

Statistical Data Analysis

The measured carbonyl VOC concentrations in exhaled breath samples were separated into healthy specimen control (n=193), primary cancer only (n=13), primary cancer metastatic to the lung groups (n=19) and all primary cancer patients, i.e., both primary cancer only and primary metastatic to the lung (n=32). The groups having a sufficient number of samples were analyzed by the Wilcoxon test to determine statistically significant differences between the groups. The Wilcoxon tests were performed using Minitab version 16.0.

Results and Discussion

The efficiencies of carbonyl capture by the ATM-coated preconcentrator were characterized first by using single carbonyl standards and mixtures of carbonyl standards. The capture efficiencies are affected by the velocity of the VOC mixture flowing through the preconcentrators, as well as the molar ratio of ATM/carbonyl compound. Capture efficiencies greater than 98% have been achieved for trace ketones and aldehydes under the optimized preconcentrator microstructure and operation conditions.

Prior to exhaled breath analysis, the concentrations of carbonyl VOCs from laboratory air, clinic room air, and street air samples were determined. Then, the concentrations of carbonyl VOCs in exhaled breath samples from 193 healthy (healthy specimens) controls and 32 patients (subject specimens) with primary cancers originating outside of the lung were measured. The patients with primary cancers were subdivided into groups in which the primary cancer had metastasized to the lung (melanoma, colon cancer, breast cancer, renal cancer, pancreatic cancer, prostate cancer, ovarian cancer, cholangiocarcinoma, lymphoma, and squamous skin cancer) and groups in which no metastatic cancer was identified in the lung (esophageal cancer, squamous cell supra glottis cancer, mesothelioma, chondrosarcoma, and pancreatic cancer). Carbonyl-containing VOCs from C1 (formaldehyde) to C12 in the exhaled breath samples of the healthy subjects and the patients with primary cancers originating outside of the lung have been detected (both primary cancer only and primary metastatic to the lung).

This represents a broad range of oncologic cell types and tissues of origin. To explain the data more carefully—when compared to a cohort of 193 control patients, each patient with cancer had at least one carbonyl compound that is present at levels greater than two standard deviations above the levels identified in the control population. This is represented in the graphs of FIGS. 3-6, each of which represents the values for one of the four different markers, i.e., $C_4H_8O$ (FIG. 3), $C_2H_4O_2$ (FIG. 4), $C_4H_8O_2$ (FIG. 5), and 4-HHE (FIG. 6), for a variety of cancers. The left most bar in each graph is the mean value for the control population (with error bars representing the standard deviation), while the remaining bars are the values for the patients with the indicated cancers.

Also, as illustrated in Tables 2 and 3 below, all of the subjects with each type of cancer had elevated values for at least one of the four different markers and a majority had elevated levels of at least two different markers.

TABLE 2

Percentage of subjects having at least 1, 2, or 3 elevated markers

| Compounds Distribution | N | 1 or more | 2 or more | 2 or more |
|---|---|---|---|---|
| Total other cancers | 32 | 93.70% | 65.60% | 40.60% |
| Primary Cancer (No METS) | 13 | 84.60% | 61.50% | 38.40% |
| Metastasis to Lung (METS) | 19 | 100% | 68.40% | 42.10% |

TABLE 3

Exemplary data of elevated levels of markers in subjects with a wide range of primary cancer types

| | N | $C_4H_8O$ | $C_2H_4O_2$ | $C_4HO_8O_2$ | 4-HHE | 1 or more | 2 or more | 2 or more |
|---|---|---|---|---|---|---|---|---|
| Distribution Primary | | | | | | | | |
| Esophageal Squamous Cell | 9 | 66.70% | 66.70% | 66.70% | 33.30% | 100% | 66.70% | 44.40% |
| Supra Glottis | 1 | | | | | 100% | 100% | 100% |
| Mesothelioma | 1 | | | | | 0 | 0 | 0 |
| Chondrosarcoma | 1 | | | | | 0 | 0 | 0 |
| Pancreatic | 1 | | | | | 100% | 100% | 0 |
| Distribution METS | | | | | | | | |
| Melanoma | 4 | 50% | 25% | 75% | 50% | 100% | 50% | 50% |
| Colon Cancer | 5 | 60% | 40% | 100% | 20% | 100% | 60% | 40% |
| Breast | 2 | | | | | 100% | 100% | 50% |
| Renal | 2 | | | | | 100% | 100% | 50% |
| Pancreas | 1 | | | | | 100% | 100% | 0 |
| Prostate | 1 | | | | | 100% | 100% | 100% |
| Ovarian | 1 | | | | | 100% | 0% | 0 |
| Cholangiocarcinoma | 1 | | | | | 100% | 100% | 0% |
| Lymphoma | 1 | | | | | 100% | 0% | 0 |
| Squamous Skin | 1 | | | | | 100% | 100% | 100% |

While the present invention has been illustrated by the description of embodiments, and while the illustrative embodiments have been described in considerable detail, it is not the intention of the inventors to restrict or in any way limit the scope of the appended claims to such detail. Additional advantages and modifications readily will appear to those skilled in the art. The invention in its broader aspects is therefore not limited to the specific details, representative apparatus and methods, and illustrative examples shown and described. Accordingly, departures may be made from such details without departing from the scope of the inventors' general inventive concept.

What is claimed is:

1. A non-invasive method of detecting a cancer disease state in a subject specimen wherein a primary cancer originates in a tissue outside of the lung and has not metastasized to the lung, the method comprising the steps of:
    obtaining exhaled breath from the subject specimen, wherein the exhaled breath includes a plurality of carbonyl-containing volatile organic compounds (VOCs);
    forming adducts of the plurality of carbonyl-containing VOCs with a reactive chemical compound;
    quantifying each of the adducts of each of the plurality of carbonyl-containing VOCs to establish a subject value for each of the adducts; and
    comparing each subject value to a threshold healthy specimen value for each of the adducts of the plurality of carbonyl-containing VOCs, the threshold healthy specimen value corresponding to a value calculated from healthy specimens, in order to determine the presence of one or more subject values at quantities greater than their respective threshold healthy specimen values, thereby indicating a substantial likelihood of a cancer disease state in the subject specimen;
    wherein the plurality of carbonyl-containing VOCs includes 2-pentanone or pentanal, and includes at least one VOC selected from the group consisting of 2-butanone, 2-hydroxyacetaldehyde, 3-hydroxy-2-butanone, and 4-hydroxy-2-hexenal.

2. The method of claim 1, wherein the cancer disease state is selected from the group consisting of supraglottic squamous cell carcinoma, pancreatic cancer, melanoma, colon cancer, breast cancer, renal cell carcinoma, prostate cancer, ovarian cancer, esophageal cancer, chondrosarcoma, cholangiocarcinoma, lymphoma, and squamous skin cancer.

3. The method of claim 1, wherein the cancer disease state is selected from the group consisting of supraglottic squamous cell carcinoma, pancreatic cancer, esophageal cancer, mesothelioma, and chondrosarcoma.

4. The method of claim 1, further comprising:
concentrating the plurality of carbonyl-containing VOCs contained in exhaled breath obtained from a plurality of healthy specimens, wherein the plurality of carbonyl-containing VOCs obtained from the plurality of healthy specimens form adducts with the reactive chemical compound; and quantifying the adducts of the plurality of carbonyl-containing VOCs obtained from the plurality of healthy specimens to establish the threshold healthy specimen values for each of the adducts of the plurality of carbonyl-containing VOCs.

5. The method of claim 1, wherein obtaining exhaled breath from the subject specimen comprises collecting the exhaled breath in an inflatable, polymeric film device to provide an inflated device comprising a breath sample; and wherein forming adducts of the plurality of carbonyl-containing VOCs with a reactive chemical compound comprises passing the breath sample through a chemical preconcentrator comprising the reactive chemical compound.

6. The method of claim 5, wherein passing the breath sample through a chemical preconcentrator comprises connecting the inflated device to an inlet of the chemical preconcentrator, and applying reduced pressure to an outlet of the chemical preconcentrator to induce flow of the breath sample from the inflated device through the chemical preconcentrator.

7. The method of claim 1, wherein the reactive chemical compound has a general formula (I) of:

$$H_2N-Z-L-Y, \quad (I)$$

wherein Z is NH, NR or O; L is a linking group; Y is a di-substituted or tri-substituted nitrogen or phosphorous; R is selected from the group consisting of alkyls, aralkyls, aralkenyls, and aralkynyls, each of which may be substituted or unsubstituted, and optionally contain one or more heteroatoms, and wherein the plurality of carbonyl-containing VOCs react with the reactive chemical compound via a dehydration reaction to form adducts thereof.

8. The method of claim 7, wherein Z is O, and Y is a di-substituted or tri-substituted nitrogen to provide the reactive chemical compound having a general formula (II)

(II)

wherein $R^1$ and $R^2$ are independently selected from the group consisting of alkyls, aralkyls, aralkenyls, and aralkynyls, each of which may be substituted or unsubstituted, and optionally contain one or more heteroatoms, or wherein $R^1$ and $R^2$ in combination form a heterocyclic ring; $R^3$ is selected from the group consisting of H, alkyls, aralkyls, aralkenyls, and aralkynyls, each of which may be substituted or unsubstituted, and optionally contain one or more heteroatoms; and A is an anionic counter-ion; and wherein said linking group L comprises a non-ionic segment selected from the group consisting of a substituted or unsubstituted alkyl, a substituted or unsubstituted aryl, and an ether.

9. The method of claim 7, wherein Z is O, and Y is a di-substituted nitrogen to provide the reactive chemical compound having a general formula (III)

(III)

wherein $R^1$ and $R^2$ are independently selected from the group consisting of alkyls, aralkyls, aralkenyls, and aralkynyls, each of which may be substituted or unsubstituted, and optionally contain one or more heteroatoms, or wherein $R^1$ and $R^2$ in combination form a heterocyclic ring.

10. The method of claim 1, wherein the reactive chemical compound is a 2-(aminooxy)-N,N,N-trimethylethanammonium salt.

11. The method of claim 1, wherein quantifying each of the adducts comprises analyzing each of the adducts using a mass spectrometer.

12. The method of claim 11, wherein the mass spectrometer uses Fourier-transform ion cyclotron resonance mass spectrometry (FTICR-MS).

13. The method of claim 11, wherein the mass spectrometer is coupled with a chromatography apparatus.

14. A non-invasive method of screening for a cancer disease state in a subject specimen wherein a primary cancer originates in a tissue outside of the lung and has not metastasized to the lung, the method comprising the steps of:
concentrating a plurality of carbonyl-containing volatile organic compounds (VOCs) contained in exhaled breath obtained from the subject specimen, wherein the plurality of carbonyl-containing VOCs includes 2-pentanone or pentanal, and includes at least one VOC selected from the group consisting of 2-butanone, 2-hydroxyacetaldehyde, 3-hydroxy-2-butanone, and 4-hydroxy-2-hexenal, which form adducts with a reactive chemical compound;
forming adducts of the plurality of carbonyl-containing VOCs with a reactive chemical compound;
quantifying the adducts of the plurality of carbonyl-containing VOCs to establish a subject value for each member of the adducts of the plurality of carbonyl-containing VOCs; and
comparing the subject value for each member of the adducts of the plurality of carbonyl-containing VOCs to a threshold healthy specimen value for each member of the adducts of the plurality of carbonyl-containing VOCs to determine the presence of one or more carbonyl containing VOCs at quantities greater than its respective threshold healthy specimen value thereby indicating a substantial likelihood of the cancer disease state in the subject specimen.

\* \* \* \* \*